United States Patent [19]

Stead et al.

[11] 4,405,818

[45] Sep. 20, 1983

[54] PRODUCTION OF META-ISOPROPYLPHENOLIC PRODUCTS

[75] Inventors: George E. Stead, Piscataway; Lewis B. Young, Skillman, both of N.J.

[73] Assignee: Mobil Oil Corporation, New York, N.Y.

[21] Appl. No.: 307,049

[22] Filed: Sep. 30, 1981

[51] Int. Cl.³ .................. C07C 37/14; C07C 39/06
[52] U.S. Cl. .................................................. 568/781
[58] Field of Search .............. 568/781, 783, 806, 805

[56] References Cited

U.S. PATENT DOCUMENTS

| | | | |
|---|---|---|---|
| 3,014,079 | 12/1961 | Olin | 568/783 |
| 4,181,811 | 1/1980 | Young | 585/486 |
| 4,197,413 | 4/1980 | Kaeding et al. | 568/798 |
| 4,205,189 | 5/1980 | Young et al. | 568/768 |
| 4,230,894 | 10/1980 | Young | 568/768 |
| 4,242,528 | 12/1980 | Kato et al. | 568/806 |
| 4,283,571 | 8/1981 | Keim et al. | 568/783 |

FOREIGN PATENT DOCUMENTS

| | | | |
|---|---|---|---|
| 12570 | 6/1980 | European Pat. Off. | |
| 2139622 | 2/1973 | Fed. Rep. of Germany | 568/781 |

*Primary Examiner*—Werren B. Lone
*Attorney, Agent, or Firm*—Charles A. Huggett; Michael G. Gilman; George W. Allen

[57] ABSTRACT

Organic compound mixtures enriched in meta-isopropylphenol are prepared by alkylating phenol with isopropanol or propylene to form mixtures of isopropylphenol isomers and by subsequently selectively cracking the para-isopropylphenol isomer from such a mixture over a ZSM-5 type cracking catalyst. Concentration of the para-isomer is thereby selectively reduced relative to the meta-isomer and the meta-isopropylphenol isomer can be further separated from the remaining mixture by fractionation procedures.

13 Claims, No Drawings

PRODUCTION OF META-ISOPROPYLPHENOLIC PRODUCTS

BACKGROUND OF THE INVENTION

1. Field of the Invention

The present invention relates to the selective catalytic cracking of mixtures of isopropylphenol isomers in order to reduce the content of the para-isopropylphenol isomer therein and to thereby provide an isopropylphenolic product enriched in the meta-isopropylphenol isomer.

2. Description of the Prior Art

Propylated phenolic products such as meta-isopropylphenol and mixtures containing it are useful materials in the synthesis of various products such as adhesives, agricultural chemicals and pharmaceuticals. It is known to prepare such products via the alkylation of phenolic compounds with such propylating agents as propylene and isopropanol, and a variety of alkylation catalysts are known to promote such a reaction. For example, U.S. Pat. Nos. 3,959,394; 3,439,048; 3,426,358; 3,426,082; 3,409,678; 3,382,283; 3,367,981; 3,265,742; 3,185,737; 3,133,974; 3,082,258 and 3,071,595, all disclose alkylation of phenols over a variety of catalyst such as Friedel Crafts catalysts ($AlCl_3$, HF, $BF_3$, etc.), zinc halides, alumina, aluminum phenoxide, alkane sulfonic acids and the like. Although many of these reactions are said to favor formation of the ortho-alkylphenols, reaction products in all instances contain at least some of the para- and meta-isomers as well.

Separation of the desired meta-isomer of propylated phenolic compounds from mixtures which also contain the para isomer of isopropylphenol is difficult to accomplish using conventional fractionation techniques since the boiling points of these two isomers are so close. There is thus a need to identify phenolic compound synthesis process procedures, conditions and catalysts which can be used to selectively prepare mixtures containing maximized amounts of desirable meta-isopropylphenolic compounds. Accordingly, it is an object of the present invention to provide a process for producing a product mixture comprising increased concentrations of the meta-isomer of isopropylated phenol.

SUMMARY OF THE INVENTION

In accordance with the present invention, there is provided a process for preparing a product mixture enriched in meta-isopropylphenol. As a first step in such a process, phenol is alkylated with either isopropanol or propylene under alkylation conditions to produce an alkylation product containing isopropylphenol isomers. As a second process step, a mixture containing both meta- and para-isopropylphenol from this alkylation product is contacted with a particular zeolite catalyst under certain reaction conditions to selectively reduce, e.g., by cracking, the concentration of para-isopropylphenol in the mixture relative to the concentration of meta-isopropylphenol. The catalyst employed in such a catalytic cracking step is a crystalline zeolite material having a silica to alumina mole ratio of at least about 12 and a constraint index within the approximate range of 1 to 12. Cracking conditions employed include a reaction temperature of from about 150° to 600° C. and a reaction pressure of from about $10^4$ N/M$^2$ to $10^6$ N/m$^2$.

DETAILED DESCRIPTION OF THE INVENTION

The two essential steps of the process herein involve (a) alkylation of phenol with a propylating agent to produce a mixture of isopropylphenol isomers and (b) selective cracking of the para-isopropylphenol isomer from this mixture over a particular type of crystalline zeolite catalyst. The reamining isopropylphenolic mixture can then be fractionated to recover therefrom a product enriched in meta-isopropylphenol.

The initial alkylation step of such a procedure is conducted by reacting phenol (hydroxybenzene) and a particular type of alkylating agent. The alkylating agent used in the process of the present invention is one which provides the isopropyl isomer of the propylated phenol product produced. Thus, the alkylating agent used herein can be selected from isopropanol or propylene and can be employed in a molar ratio of phenol to alkylating agent of from about 20:1 to 0.5:1, preferably from about 10:1 to 2:1. The isopropanol or propylene alkylating agent may be utilized as the pure compound or may be admixed with one or more inert diluents as hereinafter more fully described.

Alkylation of phenol with the isopropanol or propylene alkylating agent can be conducted under conventional alkylation conditions. Thus, contact of phenol and alkylating agent generally is carried out at temperatures of from about 150° C. to 600° C., preferably from about 200° C. to about 400° C., and at pressures ranging from about $10^3$ to $10^7$ N/m$^2$, preferably from about $10^4$ to $10^6$ N/m$^2$.

Alkylation conditions may also include utilization of an alkylation catalyst. Various catalysts suitable for promoting the propylation of phenol are known in the art. Such materials include those which may be broadly defined as being Lewis and Bronsted acids. A partial listing of materials known to catalyze alkylation of aromatics, which is not intended to be comprehensive of all the catalytic materials utilizable herein, would include: $AlCl_3$; $AlCl_3.HCl$; $AlCl_3.H_2O$; $AlBr_3$; $FeCl_3$; $SnCl_4$; $TiCl_4$; $ZrCl_4$; $BF_3$-$Et_2O$; $PF_5$; $H_2SO_4$; alkane sulfonic acids such as $CH_3SO_3H$; Amberlyst-15 (ion exchange resin); $P_2O_5$; $H_3PO_4$/kieselguhr; $SiO_2.Al_2O_3$; $BF_3.Al_2O_3$; $EtAlCl_2.H_2O$; alumina; aluminum phenoxide; crystalline zeolites; nickel molybdate; calcium dihydrogen phosphate; and the like. A more complete exposition of alkylation catalysts utilizable in the alkylation step of the hereindisclosed process, along with discussion of suitable reaction parameters for each, may be found in the treatise by G. A. Olah entitled *Friedel-Crafts and Related Reactions*. Vol. II (published by Interscience, 1963).

Alkylation of phenol over such catalysts provides various mixtures of isopropylphenol isomers with the isomeric distribution depending upon the selectivity properties of the particular catalyst employed and upon reaction conditions. Catalysts which provide relatively higher concentrations of the meta-isopropylphenol isomer in the reaction product are preferred for use in the alkylation step of the present invention. Catalysts such as silica-alumina, for example, can provide isopropylphenol mixtures containing the approximate isomeric distribution of about 25% para; 25% ortho; and 50% meta. If a catalyst is employed to promote alkylation, the weight hourly space velocity (WHSV) can generally vary between about 0.01 and 1000, more preferably from about 0.1 to 100.

The alkylation step of the instant process may be carried out as a batch type, semi-continuous or continuous process with the reactants in either liquid or vapor phase. Furthermore, the feed stream of reactants to the alkylation reaction zone may optionally comprise inert materials such as diluents or solvents. Suitable inert materials include nitrogen, carbon dioxide, water, carbon monoxide, helium, hydrogen, methane, etc.

Upon completion of the alkylation step to the extent desired, the resulting first reaction mixture, i.e., the alkylation reaction product, contains various amounts of meta- and para-isopropylphenol isomers generally along with ortho-isopropylphenol, unreacted phenol and other biproducts, and/or diluents. In accordance with the present invention, this alkylation reaction product or a mixture derived therefrom containing the meta- and para-isopropylphenol isomers, can be contacted with a particular type of zeolite catalyst under certain reaction conditions to selectively reduce the concentration of the para-isopropylphenol isomer within the alkylation reaction product relative to the meta-isopropylphenol isomer therein. Such a reduction in para-concentration is believed to result from the cracking of the para-isopropylphenol isomer into its phenol and propylene constituents with such reaction being relatively selective to para-isomer cracking in preference to cracking of the meta- and ortho-isomers as well as to other reactions.

The cracking step of the present process is conducted in the present process in the presence of a particular type of crystalline zeolite catalyst which promotes selective cracking of the para-isopropylphenol isomer. Such crystalline zeolites are members of a special class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 and preferably at least 30 are useful, it is also preferred in some instances to use zeolites having substantially higher silica/alumina ratios, e.g., 1600 and above. In addition, zeolites as otherwise characterized herein but which are substantially free of aluminum, that is, zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity), but which otherwise embody the characteristics disclosed.

Members of this particular class of zeolites, after activation, acquire an intracrystalline sorption capacity for normal hexane which is greater than that for water, i.e., they exhibit "hydrophobic" properties. The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Beta | 0.6 |
| ZSM-4 | 0.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the special class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, ZSM-48 and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particulary described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

ZSM-48 is more particularly described in published European patent application No. 80 300,463, the entire content of which is incorporated herein by reference.

It is to be understood that by incorporating by reference the foregoing patents and application to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents and application should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint," which establishes the indentity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites include are ZSM-5, ZSM-11, ZSM-12, ZSM-23, ZSM-35, ZSM-38, and ZSM-48, with ZSM-5, ZSM-11 and ZSM-23 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired.

Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article on Zeolite Struture by W. M. Meier. This paper, the entire contents of which are incorporated herein by reference, is included in "Proceedings of the Conference on Molecular Sieves, London, April 1967," published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The size of the zeolite crystals employed in the cracking step catalyst can also affect the selective cracking properties of such a catalyst. For highest selectivity to para-isomer cracking, it is preferred that the size of the zeolite crystals utilized range from about 0.01 to 5 microns, more preferably from about 0.1 to 2 microns.

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the selective cracking step of the present invention, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

Reaction conditions employed in carrying out the cracking step over the catalyst as hereinbefore described include temperatures of between about 150° C. and 600° C., pressures of between about 10 N/m about $10^6$ N/m$^2$ (0.1 to 10 atmospheres) and a feed weight hourly space velocity (WHSV) of between about 0.1 and about 10. The latter WHSV is based upon the weight of the catalyst compositions, i.e. the total weight of active catalyst and binder therefor. It is preferred that contact between the catalyst and the mixture of isomers from the alkylation step be carried out at from about 300° C. to about 450° C., and a WHSV of from about 1 to 5. Although the cracking reaction normally takes place at atmospheric pressure, the preferred pressure range extends from about $5 \times 10^4$ to about $2 \times 10^5$ N/m$^2$ (0.5 to 2 atmospheres).

The feed to the cracking step of the present process can comprise various mixtures of the meta and para isopropylphenol isomers which have been formed during the alkylation step of the present invention. Although these isomers can be separated from the alkylation product before being fed to the selective cracking step, it is preferred to introduce the complete alkylation product mixture to the cracking zone without separating it into its individual isopropylphenolic or other components.

The cracking step of this invention may also be carried out as a batch-type, semi-continuous or continuous operation utilizing a fixed, fluidized or moving bed catalyst system. A preferred embodiment entails use of a fluidized catalyst zone wherein the reactants, i.e. the isomeric mixture from the alkylation step which contains isopropylphenol isomers and unreacted phenol, is passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the reaction zone for further contact with the aromatic reactants.

The cracking step, like the alkylation step, may be carried out in a system wherein the reactants are in either the liquid or the vapor state, and the feed stream for the cracking step may also contain other inert materials as diluents or solvents. As with the alkylation step, suitable diluents include, but are not limited to: nitrogen, carbon dioxide, water, carbon monoxide, helium, hydrogen, etc. It has been surprisingly discovered that utilization of a diluent in connection with the selective para-isomer cracking step can preserve catalyst life and enhance catalyst activity. For these reasons, the use of a diluent is preferred with the preferred diluent being nitrogen.

The selective cracking step of the present invention can be carried out in one stage or in a plurality of stages. It is preferred, however, to conduct the cracking step in two or more stages, and to separate the cracking gases, primarily propylene, from the reaction stream between stages. Such propylene containing cracking gases can be recycled to the alkylation step of the present process for use as propylating agent.

Upon completion of the selective cracking step to the desired extent, the effluent from the cracking reaction zone comprises a mixture enriched in meta- and possibly ortho-isopropylphenol isomers by virtue of the selective removal from the mixture of the para-isopropylphenol isomer. An optional additional step of the process herein involves the conventional fractionation of this cracking zone effluent in order to separate the mixture into various desired components. Thus, by distilling the cracking step effluent which is depleted in the para-isomer, this mixture can be separated into streams comprising phenol (B.P.=182° C.), ortho-isopropylphenol (B.P.=214°-5° C.) and meta-isopropyphenl (B.P.=228° C.). Phenol recovered in this manner can be recycled to the alkylation step of the process.

The following examples illustrate the process of the present invention but are not limiting thereof.

EXAMPLE I

Phenol is alkylated with isopropanol alkylating agent in the presence of an amorphous aluminosilicate alkylation catalyst having an $SiO_2/Al_2O_3$ molar ratio of about 90/10. Using an alkylation temperature of about 300° C., a pressure of about $10^5$ $N/m^2$, a molar ratio of alkylating agent to phenol of about 1:1 and a WHSV of about 1, an alkylation product is produced comprising about 73 mole % phenol; and 27 mol % of a mixture of propyphenols containing some methyl- and ethylphenols. The isomer ratios of the isopropylphenols in such a product mixture is about 30% ortho, 50% meta and 20% para.

A mixture of isopropylphenol isomers approximating the ratios of these materials in the foregoing alkylation product mixture is contacted with 3 grams of an HZSM-5 zeolite catalyst at a temperature of about 350° C. and a pressure of about $10^5$ $N/m^2$. The zeolite employed as a catalyst has a crystal size of about 0.5 micron and is used without a binder. Nitrogen is added to the feed at the rate of about 30 ml/min. Feed and product composition, flow rates for the organic reactants, and conversion results for such a reaction are shown in Table I.

TABLE I

| Component | Feed (Mol %) | Product (Mol %) 4.4 ml/hr | Product (Mol %) 8.8. ml/hr | Conversion (Mol %) 4.4 ml/hr | Conversion (Mol %) 8.8 ml/hr |
|---|---|---|---|---|---|
| Phenol | 0.72 | 40.9 | 31.5 | | |
| m-isopropylphenol | 55.6 | 39.6 | 46.1 | 28.8 | 17.0 |
| o-isopropylphenol | 19.0 | — | — | 13.5 | 6.6 |
| p-isopropylphenol | 24.7 | 1.6 | 3.7 | 93.7 | 85.2 |

The Table I data indicate that from a mixture of these isopropylphenol isomers, the para-isomer is selectively cracked over the particular zeolite catalyst used.

EXAMPLE II

In a manner similar to the procedure of Example I, phenol is alkylated with an isopropanol alkylating agent in the presence of an amorphous aluminosilicate alkylation catalyst. Using reaction conditions approximately identical to those of the Example I alklation procedure, an alkylation product containing phenol and isopropylphenol is produced.

A mixture of phenol and isopropylphenol isomers approximating the ratios of these materials in such a alkylation product mixture is contacted with 3 grams of HZSM-5 zeolite catalyst (crystal size=0.5 micron) under reaction conditions substantially similar to those set forth in Example I. Again nitrogen is added to the feed at the rate of about 30 ml/min. Feed and product composition, flow rates for the organic reactants and conversion results for such a reaction are shown in Table II.

TABLE II

| Component | Feed (Mol %) | Product (Mol %) 4.4 ml/hr | Product (Mol %) 8.8. ml/hr | Conversion (Mol %) 4.4 ml/hr | Conversion (Mol %) 8.8 ml/hr |
|---|---|---|---|---|---|
| Phenol | 58.5 | 73.0 | 70.2 | | |
| m-isopropylphenol | 23.1 | 16.5 | 18.8 | 28.8 | 18.6 |
| o-isopropylphenol | 8.0 | — | — | 11.1 | 8.9 |
| p-isopropylphenol | 10.4 | 1.0 | 1.95 | 90.1 | 81.2 |

The Table II data indicate that selective cracking of the para-isopropylphenol isomer occurs over an HZSM-5 catalyst even when the mixture of isomers being reacted also contains a substantial amount of phenol.

EXAMPLE III

In a manner similar to the procedures of Examples I and II, phenol is alkylated with an isopropanol alkylating agent in the presence of an amorphous aluminosilicate alklation catalyst. Using reaction conditions substantially equivalent to those of the Examples I and II alkylation procedure, an alkylation product containing phenol and isopropylphenol is produced.

A mixture of meta and para isopropylphenol isomers approximating the ratios of these materials in such an alkylation product mixture is contacted with 3 grams of HZSM-5 zeolite catalyst (crystal size=0.5 micron) under reaction conditions substantially similar to those set forth in Examples I and II. As in those examples, nitrogen is added to the feed at the rate of about 30 ml/min. Feed the product composition, flow rates for the organic reactants and conversion results for such a reaction are shown in Table III.

TABLE III

| Component | Feed (Mol %) | Product (Mol %) 4.4 ml/hr | Product (Mol %) 8.8. ml/hr | Conversion (Mol %) 4.4 ml/hr | Conversion (Mol %) 8.8 ml/hr |
|---|---|---|---|---|---|
| Phenol | — | 43.3 | 33.5 | | |
| m-isopropylphenol | 67.8 | 51.6 | 58.8 | 23.9 | 13.2 |
| o-isopropylphenol | — | — | — | — | — |
| p-isopropylphenol | 32.2 | 2.6 | 6.2 | 92.1 | 80.8 |

The Table III data indicate that p-isopropylphenol is selectively cracked from mixtures comprising only meta- and para isomers of isopropylphenol.

EXAMPLE IV

In a manner similar to the procedures of Examples I, II and III, phenol is alkylated with an isopropanol alkylating agent in the presence of an amorphous aluminosilicate alkylation catalyst. Using reaction conditions substantially equivalent to those of the Examples I, II and III alkylation procedure, an alkylation product containing phenol and isopropylphenol is produced.

A mixture of meta and para isopropylphenol isomers approximating the ratios of these materials in such an alkylation product mixture is contacted with 3 grams of an HZSM-12 catalyst (no binder) at atmospheric pressure and at a flow rate of organic reactants of 4.4 ml/hr. Runs at both 400° C. and 450° C. are made. Nitrogen is added to the feed at the rate of 30 ml/min.

Feed and product composition and conversion results for such a reaction are shown in Table IV.

TABLE IV

| | Feed | Product 400° C. | Product 400° C. | Product 450° C. | Product 450° C. | Product 450° C. |
|---|---|---|---|---|---|---|
| Component (Mol %) | | | | | | |
| Phenol | — | 25.3 | 22.9 | 59.7 | 57.9 | 47.4 |
| m-Isopropylphenol | 67.8 | 55.7 | 57.1 | 29.9 | 31.9 | 39.3 |
| p-Isopropylphenol | 32.2 | 16.1 | 17.2 | 7.6 | 7.9 | 10.5 |
| Conversion (%) | | | | | | |
| m-Isopropylphenol | | 17.9 | 15.8 | 55.8 | 53.0 | 42.1 |
| p-Isopropylphenol | | 49.9 | 46.7 | 76.4 | 75.4 | 67.4 |
| % $\left(\frac{\text{m-Isopropylphenol}}{\text{m + p-Isopropylphenol}}\right)$ | | 77.5 | 76.9 | 79.8 | 80.1 | 78.9 |

The Table IV data demonstrate that ZSM-12 is not as selective with respect to cracking of p-isopropylphenol as is smaller pore (as judged by Constraint Index) ZSM-5. ZSM-12 is, however, still significantly more selective with respect to para-isomer vs. meta-isomer cracking than is a non-shape selective catalyst.

EXAMPLE V

To demonstrate the beneficial effect of utilizing an inert diluent in the selective cracking step of the process of the present invention, a mixture of meta- and para-isopropylphenol, in ratios approximating those which might result from the alkylation of phenol with isopropanol or propylene, is reacted over an HZSM-5 catalyst, with and without nitrogen present in the feed. Cracking conditions are essentially identical to those employed in the cracking steps of Examples I, II and III. Thus, the reaction mixture is contacted with 3 grams of HZSM-5 (crystal size=0.5 micron, no binder) at 350° C. and atmospheric pressure. Nitrogen, when employed, is introduced at 30 ml/min. Feed and product composition, flow rates for the organic reactants and conversion results for such a cracking step are shown in Table V.

TABLE V

| Component | Feed Mol % | Product (Mol %) 4.4 ml/hr No N$_2$ | Product (Mol %) 4.4 ml/hr N$_2$ | Product (Mol %) 8.8 ml/hr No N$_2$ | Product (Mol %) 8.8 ml/hr N$_2$ | Conversion (Mol %) 4.4 ml/hr No N$_2$ | Conversion (Mol %) 4.4 ml/hr N$_2$ | Conversion (Mol %) 8.8 ml/hr No N$_2$ | Conversion (Mol %) 8.8 ml/hr N$_2$ |
|---|---|---|---|---|---|---|---|---|---|
| Phenol | — | 28.9 | 43.3 | 16.5 | 33.5 | — | — | — | — |
| m-Isopropylphenol | 67.8 | 59.8 | 51.6 | 65.2 | 58.8 | 11.8 | 23.9 | 3.9 | 13.2 |
| p-Isopropylphenol | 32.2 | 10.1 | 2.6 | 18.3 | 6.2 | 68.8 | 92.1 | 43.2 | 80.8 |

The Table V data demonstrate that the presence of nitrogen in the feed to the cracking step significantly reduces the amount of p-isopropylphenol in the reaction product, i.e. significantly increases the conversion of p-isopropylphenol present in the feed. While addition of nitrogen also somewhat increases the amount of m-isopropylphenol reacted, the cracking reaction is still highly selective to the para-isopropylphenol isomer.

EXAMPLE VI

To demonstrate the effect of zeolite crystal size in the selective cracking step of the process of the present invention, a mixture of meta and para-isopropylphenol, in ratios approximating those which might result from the alkylation of phenol with isopropanol or propylene is reacted over several samples of HZSM-5 catalyst, at varying flow rates, temperatures and zeolite crystal sizes. The reaction mixture is contacted with 3 grams of HZSM-5 (no binder) at both 300° C. or 350° C. and at atmospheric pressure. Nitrogen is introduced at the rate of 30 ml/min. Feed and product composition reaction temperatures, flow rates for the organic reactants and conversion results for such a cracking step are shown in Table VI.

TABLE VI

| | | Product | | | | |
| --- | --- | --- | --- | --- | --- | --- |
| | | Large Crystal HZSM-5 (~0.1-2.0μ) | | Small Crystal HZSM-5 (~0.02-0.1μ) | | |
| | Feed | 4.4 ml/hr | 8.8 ml/hr | 4.4 ml/hr | 8.8 ml/hr | 8.8 ml/hr |
| Component (Mol %) | | | | | | |
| Phenol | | 43.3 | 33.5 | 35.9 | 44.6 | 53.5 |
| m-Isopropylphenol | 67.8 | 51.6 | 58.8 | 57.2 | 47.5 | 43.6 |
| p-Isopropylphenol | 32.2 | 2.6 | 6.2 | 6.8 | 4.0 | 3.0 |
| Conversion, % | | | | | | |
| m-Isopropylphenol | | 23.9 | 13.3 | 15.6 | 29.9 | 35.6 |
| p-Isopropylphenol | | 91.9 | 80.8 | 78.9 | 87.6 | 90.7 |
| % ( meta / (meta + para) ) | | 95.2 | 90.5 | 89.4 | 92.2 | 93.6 |
| Temperature (°C.) | | 350 | 350 | 300 | 350 | 325 |

The Table VI data demonstrate that both large and small crystal HZSM-5 zeolite provide highly selective cracking of the para-isopropylphenol isomer in preference to cracking of meta-isopropylphenol.

What is claimed is:

1. A process for producing a meta-isopropylphenol-containing product mixture, said process comprising:
   (A) alkylating phenol with an alkylating agent selected from propylene and isopropanol under alkylation conditions which include a temperature of from about 150° C. to 600° C. and a pressure of from about $10^3$ N/m$^2$ to $10^7$ N/m$^2$, to produce an alkylation product comprising isomers of isopropylphenol, and
   (B) contacting a mixture containing meta and para isopropylphenol isomers from said alkylation product, with a crystalline zerolite catalyst having a silica-to-alumina molar ratio of at least about 12 and a constraint index within the approximate range of 1 to 12 at a temperature of from about 150° C. to about 600° C. and a pressure of from about $10^4$ N/m$^2$ to $10^6$ N/m$^2$, to thereby selectively crack para-isopropylphenol into phenol and propylene within said mixture and to thereby provide a product mixture enriched in meta-isopropylphenol relative to para-isopropylphenol.

2. A process according to claim 1 wherein alkylation conditions employed in the alkylation step include a temperature of from about 200° C. to 400° C., a pressure of from about $10^4$ N/m$^2$ to $10^6$ N/m$^2$ and the use of an alkylation catalyst.

3. A process according to claim 2 wherein said alkylation catalyst is selected from AlCl$_3$; AlCl$_3$.HCl; AlCl$_3$.H$_2$O; AlBr$_3$; FeCl$_3$; SnCl$_4$; TiCl$_4$; ZrCl$_4$; BF$_3$-Et$_2$O; PF$_5$; H$_2$SO$_4$; alkane sulfonic acids; ion exchange resins; P$_2$O$_5$; H$_3$PO$_4$/kieselguhr; SiO$_2$.Al$_2$O$_3$; BF$_3$.Al$_2$O$_3$; EtAlCl$_2$.H$_2$O; alumina; aluminum phenoxide; crystalline zeolites; nickel molybdate and calcium dihydrogen phosphate, and wherein the molar ratio of phenol to alkylating agent varies between about 0.5:1 and 20:1.

4. A process according to claim 3 wherein the zeolite catalyst employed in the cracking step is selected from ZSM-5, ZSM-11, ZSM-12, ZSM-23, ZSM35, ZSM-38 and ZSM-48; and wherein an inert diluent is co-fed with the reactants to the cracking step of the process.

5. A process according to claim 4 wherein the cracking step is carried out at a temperature of from about 300° C. to 450° C. and at a pressure of from about $5 \times 10^4$ N/m$^2$ to $2 \times 10^5$ N/m$^2$, and with a weight hourly space velocity of from about 0.1 to 10 and wherein the inert diluent is nitrogen.

6. A process according to claim 5 wherein propylene is recovered from the cracking step mixture and is recycled to the alkylation step.

7. A process according to claim 6 wherein the cracking step is conducted in two or more stages with propylene being removed from the reaction zone after each stage.

8. A process according to claim 7 wherein the zeolite cracking catalyst is ZSM-5.

9. A process according to claim 8 wherein meta-isopropylphenol is further separated from said cracking step product mixture by fractionation.

10. A process according to claim 9 wherein phenol is further separated from said cracking step product mixture by fractionation.

11. A process according to claim 10 wherein said phenol is recycled to the alkylation step.

12. A process for producing a meta-isopropylphenol-containing product mixture, said process comprising:
   (A) alkylating phenol with an alkylating agent selected from propylene and isopropanol under alkylation conditions which include a temperature of from about 150° C. to 600° C. and a pressure of from about $10^3$ N/m$^2$ to $10^7$ N/m$^2$, to produce an alkylation product comprising isomers of isopropylphenol, and
   (B) contacting a mixture comprising meta and para isopropylphenol isomers from said alkylation product, with a catalyst comprising the crystalline zeolite ZSM-5 at a temperature of from about 300° C. to about 450° C. and a pressure of from about $10^4$ N/m$^2$ to $10^6$ N/m$^2$, to thereby selectively crack para-isopropylphenol into phenol and propylene within said mixture and to thereby provide a product mixture enriched in meta-isopropylphenol relative to para-isopropylphenol.

13. A process for producing a meta-isopropylphenol-containing product mixture, said process comprising:
   (A) alkylating phenol with an alkylating agent selected from propylene and isopropanol under alkylation conditions which include a temperature of from about 150° C. to 600° C. and a pressure of from about $10^3$ N/m$^2$ to $10^7$ N/m$^2$, to produce an alkylation product comprising meta and para isomers of isopropylphenol and unreacted phenol; and
   (B) contacting said alkylation product, directly and without intermediate separation into its individual components, with a crystalline zeolite catalyst having a silica-to-alumina molar ratio of at least about 12 and a constraint index within the approximate range of 1 to 12 at a temperature of from about 150° C. to about 600° C. and a pressure of from about $10^4$ N/m² to $10^6$ N/m², to thereby selectively crack para-isopropylphenol in said alkylation product into phenol and propylene and to thereby provide a product mixture enriched in meta-isopropylphenol relative to para-isopropylphenol.

* * * * *